(12) United States Patent
Gordi et al.

(10) Patent No.: US 7,655,636 B2
(45) Date of Patent: *Feb. 2, 2010

(54) USE OF A2A ADENOSINE RECEPTOR AGONISTS

(75) Inventors: Toufigh Gordi, Sunnyvale, CA (US); Ann Walls Olmsted, Palo Alto, CA (US); Hsiao Dee Lieu, Burlingam, CA (US); Luiz Belardinelli, Palo Alto, CA (US)

(73) Assignee: Gilead Palo Alto, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/253,322

(22) Filed: Oct. 19, 2005

(65) Prior Publication Data
US 2006/0084625 A1 Apr. 20, 2006

Related U.S. Application Data

(60) Provisional application No. 60/620,577, filed on Oct. 20, 2004.

(51) Int. Cl.
*A61K 31/70* (2006.01)
(52) U.S. Cl. ....................................................... 514/46
(58) Field of Classification Search .................. 514/46; 536/27.63, 27.7
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 4,902,514 A | 2/1990 | Barclay et al. | |
| 4,956,345 A | 9/1990 | Miyasaka et al. | |
| 4,968,697 A | 11/1990 | Hutchison | |
| 4,992,445 A | 2/1991 | Lawter et al. | |
| 5,001,139 A | 3/1991 | Lawter et al. | |
| 5,032,252 A | 7/1991 | Owen et al. | |
| 5,070,877 A | 12/1991 | Mohiuddin et al. | |
| 5,189,027 A | 2/1993 | Miyashita et al. | |
| 5,270,304 A | 12/1993 | Kogi et al. | |
| 5,459,254 A | 10/1995 | Yamaguchi et al. | |
| 5,593,975 A | 1/1997 | Cristalli | |
| 5,616,345 A | 4/1997 | Geoghegan et al. | |
| 5,705,491 A | 1/1998 | Yamada | |
| 5,770,716 A | 6/1998 | Khan et al. | |
| 5,877,180 A * | 3/1999 | Linden et al. ................ 514/45 |
| 5,939,543 A | 8/1999 | Morozumi et al. | |
| 6,026,317 A | 2/2000 | Verani | |
| 6,214,807 B1 | 4/2001 | Zablocki | |
| 6,294,522 B1 | 9/2001 | Zablocki et al. | |
| 6,322,771 B1 | 11/2001 | Linden et al. | |
| 6,368,573 B1 | 4/2002 | Leung | |
| 6,403,567 B1 | 6/2002 | Zablocki | |
| 6,448,235 B1 | 9/2002 | Linden et al. | |
| 6,514,949 B1 * | 2/2003 | Linden et al. ................ 514/46 |
| 6,552,023 B2 | 4/2003 | Zablocki | |
| 6,599,283 B1 | 7/2003 | Marzilli et al. | |
| 6,605,597 B1 | 8/2003 | Zablocki et al. | |
| 6,642,210 B1 | 11/2003 | Zablocki et al. | |
| 6,677,336 B2 | 1/2004 | Zablocki et al. | |
| 6,770,634 B1 | 8/2004 | Zablocki et al. | |
| 6,855,818 B2 | 2/2005 | Zablocki et al. | |
| 7,144,872 B2 | 12/2006 | Zablocki et al. | |
| 2002/0012946 A1 | 1/2002 | Belardinelli et al. | |
| 2002/0111327 A1 | 8/2002 | Linden et al. | |
| 2002/0147174 A1 | 10/2002 | Jones et al. | |
| 2004/0038928 A1 | 2/2004 | Zablocki et al. | |
| 2004/0064039 A1 | 4/2004 | Belardinelli | |
| 2004/0127533 A1 | 7/2004 | Hart | |
| 2004/0198692 A1 | 10/2004 | Zablocki et al. | |
| 2005/0020915 A1 | 1/2005 | Belardinelli et al. | |
| 2005/0175535 A1 | 8/2005 | Belardinelli et al. | |
| 2007/0299089 A1 | 12/2007 | Belardinelli | |
| 2008/0170990 A1 | 7/2008 | Lieu et al. | |
| 2008/0213165 A1 | 9/2008 | Lieu et al. | |
| 2008/0267861 A1 | 10/2008 | Lieu et al. | |

FOREIGN PATENT DOCUMENTS

| CA | 965411 | 4/1975 |
|---|---|---|
| EP | 0 354 638 | 2/1990 |
| JP | S48-26038 | 8/1973 |
| JP HEI | 5[1993]-9197 | 1/1993 |

(Continued)

OTHER PUBLICATIONS

Xu et al., "Coronary Vasodilation by a Short Acting, Low Affinity A2A Adenosine Receptor Agonist in Anesthetized Closed Chest Dogs: A Second Generation of Coronary Artery Pharmacologica Stressor", Circulation, vol. 102, No. 18, pp. 3912 (2000).

(Continued)

*Primary Examiner*—Lawrence E Crane
(74) *Attorney, Agent, or Firm*—Swiss Tanner, P.C.

(57) ABSTRACT

The present invention relates to methods for producing coronary vasodilation with little peripheral vasodilation by administering doses of a pharmaceutical composition including regadenoson, named (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, — an adenosine $A_{2A}$ receptor agonist — to a human in an amount sufficient to increase the average coronary peak flow velocity by at least about 16.5 cm/sec.

10 Claims, No Drawings

FOREIGN PATENT DOCUMENTS

| | | |
|---|---|---|
| WO | WO 93/25677 | 12/1993 |
| WO | WO 98/52611 | 11/1998 |
| WO | WO 98/57651 | 12/1998 |
| WO | WO 99/63938 | 12/1999 |
| WO | WO 00/78778 | 12/2000 |
| WO | WO 00/78779 | 12/2000 |
| WO | WO 01/62979 | 8/2001 |
| WO | WO 2004/011010 | 2/2004 |
| WO | WO 2005/082379 | 9/2005 |

OTHER PUBLICATIONS

Iskandrian A., "Adenosine Myocardial Perfusion Imaging", The Journal of Nuclear Medicine, vol. 35, pp. 734-736 (1994).

Gao et al., "Novel Short-Acting A2A Adenosine Receptor Agonists for Coronary Vasodilation Inverse Relationship between Affinity and Duration of Action of A2A Agonists", Journal of Pharmacology and Experimental Therapeutics, vol. 928, pp. 209-218 (2001).

Marumoto, et al., "Synthesis and Coronary Vasodilating Activity of 2-Substituted Adenosines", Chem.. Pharm. Bull. 23(4): 759-774 (1975).

Marumoto, et al., "Synthesis and Enzymatic Activity of Adenosine 3',5'-Cyclic Phosphate Analogs", Chem.. Pharm. Bull. 27(4) 990-1003 (1979).

Persson, et al., "Synthesis and Antiviral Effects of 2-Heteroaryl Substituted Adenosine and 8-Heteroaryl Substituted Guanosine Derivatives", Bioorganic & Medicinal Chemistry, 3:1377-1382 (1995).

Mager, et al., "Molecular simulation applied to 2-(N'alkylidenehydrazino)- and 2-(N'-aralkylidenehydrazino) adenosine A2 Agnonists", Eur J. Med. Chem, 30:15-25 (1995).

Cristalli et al., "2-Alkynl Derivatives of Adenosine 5'-N'ethyluronamide: Selective A2 Adenosine Receptor Agonists with Potent Inhibitory Activity on Platelet Aggregation", J. Med. Chem, 37:1720-1726 (1994).

Matsuda, et al., "Nucleosides and Nucleotides. 103. 2-Alkynyladenoines: A Novel Class of Selective Adenosine A2 Receptor Agonists with Potent Antihypertensive Effects", J. Med. Chem. 35:241-252 (1992).

Glover et al. "Pharmacological Stress Thallium Scintigraphy with 2-Cyclohexylmethylidenehydrazinoadenosine", Circulation, pp. 1726-1732 (1996), V. 94.

Glover et al. "Characterization of a New, Highly Selective Adenosine A2A Receptor/Agonists with Potential Use in Pharmacologic Stress Perfusion Imaging", Circulation, vol. 110, pp. I-311 (1999), (Abstract No. 1626).

Cerqueira, "The Future of Pharmacologic Stress: Selective A2A Adenosine Receptor Agonists", American Journal of Cardiology, pp. 33D-40D (2004) , V. 94(2A), Feb. 22, 2004.

Kerensky et al., "Dose Dependent Increase in Human Coronary Blood Flow Velocity Following an IV Bolus of CVT-3146, a Novel A2A Adenosine Receptor Agonist: A Potential Agent for the Use in Pharmacological Stress Testing for Myocardial Perfusion Imaging", Circulation, Supplement II, vol. 106, p. II-618 (2002), Abstr. No. 3054.

Hendel et al., "Pharmacologic Stress SPECT Myocardial Perfusion Imaging with a Selective A2A Agonist: Results of a Pilot Study Comparing Adenosine with CVT-3146", Circulation, Supplement IV, vol. 108, p. IV-636 (2003), Abstr. No. 2892.

U.S. Appl. No. 11/522,120, filed Sep. 15, 2006, Elzein et al.

U.S. Appl. No. 11/588,834, filed Oct. 27, 2006, Zablocki et al.

Office Action issued by the USPTO for U.S. Appl. No. 09/338,327 on Jun. 20, 2000.

Response to Jun. 20, 2000 Office Action for U.S. Appl. No. 09/338,327.

Office Action issued by the USPTO for U.S. Appl. No. 09/812,176 on Jun. 5, 2001.

Response to the Jun. 5, 2001 Office Action for U.S. Appl. No. 09/812,176.

Office Action issued by the USPTO for U.S. Appl. No. 10/018,758 on May 22, 2003.

Amendment Under 37 CFR 1.111 in response to Office Action of May 22, 2003 for U.S. Appl. No. 10/018,758.

Final Office Action issued by the USPTO for U.S. Appl. No. 10/018,758 on Nov. 4, 2003.

Preliminary Amendment filed on Mar. 30, 2004 for U.S. Appl. No. 10/813,535.

Office Action issued by the USPTO for U.S. Appl. No. 10/813,535 on Nov. 23, 2005.

Response to the Nov. 23, 2005 Official Action for U.S. Appl. No. 10/813,535.

Preliminary Amendment filed on Jul. 6, 2001 for U.S. Appl. No. 09/792,617.

Office Action issued by the USPTO for U.S. Appl. No. 09/792,617 on Sep. 27, 2002.

Response to Sep. 27, 2002 Restriction Requirement for U.S. Appl. No. 09/792,617.

Office Action issued by the USPTO for U.S. Appl. No. 09/796,617 on Jan. 7, 2003.

Office Action issued by the USPTO for U.S. Appl. No. 10/614,702 on Sep. 16, 2004.

Hendel et al. "Initial Clinical Experience with Regadenoson, a Novel Selective A2A Agonist for Pharmacologic Stress Single-Photon Emission Computed Tomography Myocardial Perfusion Imaging", Journal of the American College of Cardiology, vol. 46, No. 11, pp. 2069-2075 (Dec. 6, 2005).

Korolkovas, Essentials of Molecular Pharmacology-Background for Drug Design, Wiley—Interscience, New York, NY, 1970, only pp. 266-272 supplied.

Kusmic et al., "Coronary microcirculatory vasoconstriction induced by low-flow ischemia in mouse hearts is reversed by an A2A adenosine receptor", FASEB Journal, Apr. 2007, A1227-A1228.

Koepfli et al., "Interaction of caffeine with regadenoson-induced hyperemic myocardial blood flow as measured by PET", European Heart Journal, vo. 27, No. Supp. 1, p. 175 (Aug. 2006).

Martin et al., "Pharmacology of 2-cylohexylmethylidenehydrazionoadenosine (WRC-0470), a novel, short-acting adenosine A-2A receptor agonist that produces selective coronary vasodilation", Drug Development Research, vol. 40, No. 4, pp. 313-324 (1997).

Riou et al., "Influence of propranolol, enalaprilat, verapamil, and caffeine on adenosine A(2A) receptor medicated coronary vasodilation", Journal of the American College of Cardiology, vol. 40, No. 9, pp. 1687-1690 (Nov. 6, 2002).

Swinyard et al., "Pharmaceutical Necessities," Chapter 66 in Remington's Pharmaceutical Sciences, 18th Ed., Gennaro et al. (eds.), 1990, Mack Publishing Co, Easton, PA, only pp. 1318-1319 supplied.

Zhao et al., "Effects of caffeine on coronary vasodilation and sinus tachycardia induced by Regadenoson, a novel adenosine A2A receptor agonist, in conscious dogs,"European Heart Journal, vol. 27, No. suppl. 1, p. 424, (Aug. 2006).

Zhao et al., "Caffeine attenuates the duration of coronary vasodilation and changes in hemodynamics induced by regadenoson (CVT-3146), a novel adenosine A2A receptor agonists" Journal of Cardiovascular Pharmacology, vol. 49, No. 6, pp. 369-375 (Jun. 2007).

Pending U.S. Appl. No. 12/163,099, filed Jun. 27, 2008.

* cited by examiner

USE OF A2A ADENOSINE RECEPTOR AGONISTS

This application claims benefit to the filing date of provisional application Ser. No. 60/620,577 filed on Oct. 20, 2004 the specification of which is incorporated herein by reference.

(1) FIELD OF THE INVENTION

This invention relates to myocardial imaging methods that are accomplished by administering doses of regadenoson—an adenosine $A_{2A}$ receptor agonist—to a mammal undergoing myocardial imaging.

(2) DESCRIPTION OF THE ART

Myocardial perfusion imaging (MPI) is a diagnostic technique useful for the detection and characterization of coronary artery disease. Perfusion imaging uses materials such as radionuclides to identify areas of insufficient blood flow. In MPI, blood flow is measured at rest, and the result compared with the blood flow measured during exercise on a treadmill (cardiac stress testing), such exertion being necessary to stimulate blood flow. Unfortunately, many patients are unable to exercise at levels necessary to provide sufficient blood flow, due to medical conditions such as peripheral vascular disease, arthritis, and the like.

Therefore, a pharmacological agent that increases cardiac blood flow (CBF) for a short period of time would be of great benefit, particularly one that did not cause peripheral vasodilation. Vasodilators, for example dipyridamole, have been used for this purpose in patients prior to imaging with radionuclide. Dipyridamole is a long-acting compound and frequently requires antidotes to reverse the prolonged side effects. It is an infusion rather than a bolus (like regadenoson). It is also non-selective for adenosine receptors and requires weight-based dosing.

Adenosine, a naturally occurring nucleoside, also is useful as a vasodilator. Adenosine exerts its biological effects by interacting with a family of adenosine receptors characterized as subtypes $A_1$, $A_{2A}$, $A_{2B}$, and $A_3$. Adenoscan® is a formulation of a naturally occurring adenosine. Adenoscan® has been marketed as an adjuvant in perfusion studies using radioactive thallium-201. However, its use is limited due to side effects such as flushing, chest discomfort, the urge to breathe deeply, headache, throat, neck, and jaw pain. These adverse effects of adenosine are due to the activation of other adenosine receptor subtypes other than $A_{2A}$, which mediates peripheral vasodilatory effects to bronchoconstriction of adenosine. Additionally, the short half-life of adenosine necessitates continuous infusion during the procedure, further complicating its use. Adenoscan® is contraindicated in many patients including those with second- or third-degree block, sinus node disease, bronchoconstrictive or bronchospastic lung disease, and in patients with known hypersensitivity to the drug.

Other potent and selective agonists for the $A_{2A}$ adenosine receptor are known. For example, MRE-0470 (Medco) is an adenosine $A_{2A}$ receptor agonist that is a potent and selective derivative of adenosine. WRC-0470 (Medco) is an adenosine $A_{2A}$ agonist used as an adjuvant in imaging. In general, compounds such as these have a high affinity for the $A_{2A}$ receptor, and consequently, a long duration of action, which is undesirable in imaging, and could possibly prolong the duration of side effects.

One especially potent and useful adenosine $A_{2A}$ receptor agonist is regadenoson. Regadenoson is selective for the adenosine $A_{2A}$ receptor, has a short duration of action and does not appear to require administration as a continuous infusion. Regadenoson and related compounds as well as methods for their manufacture and use in cardiac perfusion imagining are disclosed in U.S. Pat. Nos. 6,403,567, 6,642, 210, 6,214,807, and 6,770,634, as well as in published U.S. patent application Ser. Nos. 2002-0012946 and 2004-0022177 the entirety of each specification of which are incorporated herein by reference. Although regadenoson is a known compound, much remains unknown about its pharmacokinetic profile and range of potential therapeutic uses.

SUMMARY OF THE INVENTION

One aspect of this invention is a method of producing coronary vasodilation with little peripheral vasodilation comprising administering to a human a single dose of a pharmaceutical composition comprising regadenoson and at least one pharmaceutical excipient in an amount that is sufficient to increase the average coronary peak flow velocity by at least about 16.5 cm/sec.

Another aspect of this invention is a method of producing coronary vasodilation with little peripheral vasodilation comprising administering to a human a single dose of a pharmaceutical composition comprising regadenoson and at least one pharmaceutical excipient in an amount that is sufficient to increase the average coronary peak flow velocity by at least about 16.5 cm/sec wherein the pharmaceutical composition is administered by iv bolus.

Yet another aspect of this invention is a method of producing coronary vasodilation with little peripheral vasodilation comprising administering to a human a single dose of a pharmaceutical composition comprising regadenoson and at least one pharmaceutical excipient in an amount that is sufficient to increase the average coronary peak flow velocity by at least about 16.5 cm/sec wherein the pharmaceutical composition is administered in about 10 to about 20 seconds.

Still another aspect of this invention is a method of producing coronary vasodilation with little peripheral vasodilation comprising administering to a human a single dose of a pharmaceutical composition comprising regadenoson and at least one pharmaceutical excipient in an amount that is sufficient to increase the average coronary peak flow velocity by at least about 16.5 cm/sec wherein the amount of the pharmaceutical composition administered is sufficient to raise the average coronary peak flow velocity by an amount ranging from about 16.5 to about 77.0 cm/sec.

In still another aspect of this invention the single dose of pharmaceutical composition includes from about 10 to about 500 micrograms of regadenoson or alternatively includes an amount of regadenoson ranging from about 0.05 to about 60 µg/kg weight of the human.

In yet another aspect, this invention includes the step of performing myocardial perfusion imaging of the human following the administration of the single dose of the pharmaceutical composition to the human. In this aspect of the invention, at least one radionuclide may be administered to the human at a time selected from the group consisting of before the human receives the dose of pharmaceutical composition, simultaneously with the administration of the dose of pharmaceutical composition or after administering the dose of pharmaceutical composition to the human. This means the radionuclide and the single dose of the pharmaceutical composition may be administered separately to the human or simultaneously to the human. In a preferred aspect of this method, myocardium examination begins no sooner than about 1 minute after the single dose of the pharmaceutical composition is administered to the human.

DESCRIPTION OF A PREFERRED EMBODIMENT

Potent $A_{2A}$ agonists are useful as adjuncts in cardiac imaging when added either prior to dosing with an imaging agent or simultaneously with an imaging agent. Suitable imaging agents include, but are not limited to [201]Thallium or [99m]Technetium-Sestamibi, $^{99m}$Tc-teboroxime, and Technetium-99 m(III).

New and potent $A_{2A}$ agonists that increase CBF but do not significantly increase peripheral blood flow have been identified. One particularly useful $A_{2A}$ agonists is regadenoson. Regadenoson is also referred to in the literature as CVT-3146 or (1-{9-[(4S,2R,3R,5R)-3,4-dihydroxy-5-(hydroxymethyl)oxolan-2-yl]-6-aminopurin-2-yl}pyrazol-4-yl)-N-methyl-carboxamide and has the formula:

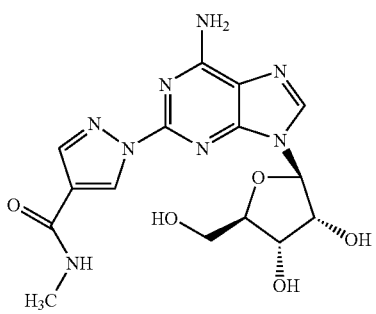

Methods for synthesizing regadenoson and related compounds are set forth in U.S. Pat. No. 6,403,567, the specification of which is incorporated herein by reference in its entirety.

Regadenoson may be administered by pharmaceutical administration methods that are known in the art. It is preferred that regadenoson is dosed i.v. It is more preferred that regadenoson is administered in a single dose i.v. The term "single dose" refers generally to a single quickly administered dose of a therapeutic amount of regadenoson. The term "single dose" does not encompass a dose or doses administered over an extended period of time by, for example continuous i.v. infusion.

Regadenoson will typically be incorporated into a pharmaceutical composition prior to use. The term "pharmaceutical composition" refers to the combination of regadenoson with at least one liquid carrier that together form a solution or a suspension. Lyophilized powders including compositions of this invention fall within the scope of "pharmaceutical compositions" so long as the powders are intended to be reconstituted by the addition of a suitable liquid carrier prior to use. Examples of suitable liquid carriers include, but are not limited to water, distilled water, de-ionized water, saline, buffer solutions, normal isotonic saline solution, dextrose in water, and combinations thereof. Such pharmaceutical compositions are generally suitable for injection.

The term "buffer solution" or "buffer" as used herein refers to a solution containing both a weak acid and its conjugate weak base. The buffer solutions are used in pharmaceutical compositions of this invention in order to resist pH changes. Non-limiting examples of useful buffer solutions are solutions that comprise sodium bicarbonate and sodium phosphate.

Pharmaceutical compounds including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compounds of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxy cellulose, acacia, polyethylene glycol, mannitol, sodium chloride, sodium citrate or any other excipient known to one of skill in the art to pharmaceutical compositions including compounds of this invention.

Pharmaceutical compositions including regadenoson may be prepared and then administered, with or without intervening storage. Various properties considered when formulating pharmaceutical compositions of this invention include, but are not limited to product shelf life, regadenoson solubility, composition pH, vein irritation, hemolysis, storage conditions (e.g., whether the pharmaceutical composition will be stored at room temperature or some other temperature) and the ability to withstand sterilization procedures.

One method to achieve the desired pharmaceutical composition properties is to include a co-solvent in the pharmaceutical composition. The co-solvent can be selected from any liquid or compound in solution that imparts the desired properties to the pharmaceutical composition. Examples of useful co-solvents include, but are not limited to methylboronic acid, borate buffer, propylene glycol, or polyethylene glycol. The amount of co-solvent in the pharmaceutical composition will depend upon properties, such as solubility and stability of the chosen $A_{2A}$ receptor agonist. Examples of pharmaceutical compositions containing co-solvents can be found in U.S. Patent Publication No. 2005/0020915, the specification of which is incorporated herein by reference in its entirety.

Regadenoson has solubility in water of about 50 micrograms/mL. Therefore, regadenoson can be dissolved and administered in water so long as the desired weight amount of regadenoson can be administered in an acceptable volume. For example, a preferred dose of about 400 micrograms can be administered in 8 mL of water. If this volume is too great for administration purposes, or if the pharmaceutical composition will be stored at other than room temperature (RT), then additional ingredients can be added to the composition to increase the solubility of regadenoson in the composition and/or to provide the resulting pharmaceutical composition with other improved properties such as improved stability and storage properties.

Pharmaceutical compositions of this invention that include regadenoson may include up to about 1 milligram/mL of regadenoson. It is preferred that pharmaceutical compositions including regadenoson include from about 50 to about 250 micrograms/mL, and more preferably from about 50 to 150 micrograms/mL of regadenoson.

In order to improve solubility and storage properties, regadenoson can be administered in a pharmaceutical composition including a methylboronic acid (MBA) co-solvent. The methylboronic acid is added to the pharmaceutical composition to improve agonist solubility and shelf life. MBA increases the pH of the resulting composition. The solubility of regadenoson in a pharmaceutical composition including MBA tends to decrease as the composition pH drops towards neutral. Therefore, with regadenoson, an optimal MBA-containing composition pH is from about 8.5 to 10 with a pH of about 9.1 to about 9.4 being preferred and a pH of about 9.3 being most preferred. This corresponds to a composition including from about 50 to about 250 mg/mL of MBA. As an alternative to MBA, regadenoson can be combined with a borate buffer solution. Typically, a borate buffer solution will be comprised of an aqueous solution of sodium borate that is adjusted to the desired pH such as a pH of 9.3 using an acid or a base.

MBA containing pharmaceutical compositions can suffer from storage problems. Namely, MBA can cause delamination when packaged in certain type I glass vessels. This problem can be overcome by storing the MBA containing pharmaceutical compositions in plastic vessels or in more resistant type I glass vessels.

If regadenoson containing pharmaceutical compositions having a pH closer to neutral are desired, then an alternative is to combine regadenoson with a propylene glycol (PG) co-solvent. The amount of PG used in the composition may range from about 5% to up to 25% by volume with a range of about 8% to about 20% by volume being more preferred when using regadenoson. An alternative to PG is polyethylene glycol—PEG. A preferred PEG will have an average molecular weight of from about 200 to 400.

Preferably, the regadenoson composition including PG or PEG will have a pH of from about 6 to about 8 with a pH of about 7 being preferred. Any physiologically acceptable buffer capable of adjusting the composition pH to the desired value can be used. Examples of such buffer include, but are not limited to, dibasic sodium phosphate, dibasic sodium phosphate dehydrate, and monobasic sodium phosphate monohydrate. Additional optional ingredients such as EDTA and dimethylacetamide could be employed in the composition as well.

The pharmaceutical compositions of this invention may include one or more anti-oxidants such as butylated hydroxyanisole (BHA).

Regadenoson has a rapid onset of action and a short duration of action when administered. Regadenoson is very useful when administered in a very small quantity in a single bolus intravenous (i.v.) injection. Regadenoson can be administered in amounts as little as 10 μg and as high as 2000 μg or more. An optimal dose may include as little as 10 μg and as much as about 1000 μg or more of regadenoson. More preferably, an optimal dose will range from about 100 to about 500 μg of regadenoson.

It is preferred that regadenoson is administered in a single bolus injection in an amount selected from about 300 μg, about 400 μg, about 500 μg, about 600 μg, and about 700 μg. These amounts are unexpectedly small when compared with adenosine which is typically administered continuously by IV infusion at a rate of about 140 μg/kg/min. Unlike adenosine, the same dosage of regadenoson can be administered to a human patient regardless of the patient's weight. Thus, the administration of a single uniform amount of regadenoson by iv bolus for myocardial imaging is dramatically simpler and less error prone than the time and weight dependent administration of adenosine. The dose of regadenoson administered to a human patient can, however, be determined by weight. Typically, a weight based dose will range from about 0.05 to about 60 μg/kg and more preferably from about 0.1 to about 30 μg/kg. Regadenoson in particular is generally well tolerated when administered in an amount up to 10 μg/kg in standing patients and up to 20 μg/kg in supine patients.

In an alternative embodiment, regadenoson may be administered orally, intravenously, through the epidermis or by any other means known in the art for administering therapeutic agents with bolus i.v. administration being preferred. In one embodiment, the bolus dosing occurs in 60 seconds or less. In yet other embodiments, the bolus dosing occurs in about 30 seconds or less, and more preferably in about 20 seconds or less or in about 10 seconds or less.

The pharmacokinetics of regadenoson are disclosed in more detail in the following examples.

EXAMPLE 1

The purpose of this study was to investigate the pharmacokinetics (PK), pharmacodynamics (PD), and the maximum tolerated dose of regadenoson in healthy human subjects.

Thirty-six healthy, male subjects were included in the study. Subjects received single, IV bolus doses of regadenoson ranging from 0.1 to 30 μg/kg. The regadenoson dosage administered in this example and in Examples 2 & 3 below was a neutral pH dose including the preferred ingredients discussed above. Concentrations of regadenoson were determined in plasma samples collected at various times and in urine samples collected over a 24-hour period after drug administration. ECG, blood pressure (BP), and heart rate (HR) were recorded for up to 24 hours post-dose. Adverse events (AE) were monitored for 24 hours post dose and via telephone 7 days later. A population approach was utilized in applying a three-compartmental PK model to the plasma concentration-time and a Michaelis-Menten model to the time-course of heart rate. The potential influence of various covariates on PK and PD model parameters was investigated.

The population value of clearance (CL) was estimated to be 40.6 Uh, with renal clearance accounting for 57% of the total clearance. The volume of distribution of regadenoson was estimated to be 83.3 L. The model estimated a baseline and a maximal increase in HR of 62 and 76 bpm. The concentration of regadenoson causing half-maximal increase in HR (potency) was estimated to be 12.4 ng/mL. Covariates such as, body mass index, body weight, age, and height had no influence on the PK or PD parameters. Adverse events were generally mild to moderate, of rapid onset, short duration, and none required medical intervention. They included abdominal discomfort, chest pressure/tightness, dizziness, dyspnea, flushing, headache, hyperventilation, nausea, palpitations, and vomiting, and increased with dose level. The maximum tolerated dose was 20 μg/kg in the supine position and 10 μg/kg in the standing position, with dose-limiting syncope or near syncope observed in subjects in the standing position.

This example demonstrates that regadenoson is well tolerated in healthy male subjects. The lack of any significant influence of the covariates on the PK and PD model parameters suggests a unit-based dosing for regadenoson.

EXAMPLE 2

The purpose of this study was to investigate the pharmacokinetics (PK) and pharmacodynamics (PD) of regadenoson in subjects undergoing clinically indicated cardiac catheterization.

Thirty-six male and female subjects undergoing clinically indicated coronary angiography were studied. Subjects received single, IV bolus doses of regadenoson ranging from 10 to 500 μg. Concentrations of regadenoson were determined in plasma samples collected at various times prior to and after drug administration. ECG, average coronary peak flow velocity (APV), measured using intracoronary Doppler flow wire, blood pressure (BP), and heart rate (HR) were continuously monitored for up to 3 hours post-dose. Occurrence of adverse events (AEs) was monitored for approximately 3 hours post dosing and via telephone approximately 14 days later. A population approach was utilized in applying PK and PD models to the plasma concentration, APV, and HR data. The potential influence of various covariates on PK and PD model parameters was investigated.

The PK data were best described by a three-compartment model. The population value of clearance and volume of distribution were estimated to be 29.9 L/h and 68.1 L, respectively. The PD model of the APV data included a hypothetical effect compartment. The baseline and the maximal increase in APV were estimated—based upon this data—to be 16.5 and 105 cm/seconds, with a potency (concentration of regadenoson that causes half maximal effect) of 29.9 ng/mL. The model estimated a small value for the distribution rate constant (4 min$^{-1}$) from the plasma to the effect site, indicating a rather rapid onset of effect. A Michaelis-Menten model resulted in the best fit of the HR data, with estimates of 67 and 41 bpm for the baseline and maximum increase in the HR, and a potency of 27.5 ng/mL. Covariates such as body mass index, body weight, age, and height had no significant influence on the PK or PD parameters. AEs were reported for fewer than half (n=17) of the subjects; events reported for 3 or more subjects were chest discomfort (n=3), tachycardia (n=4), and bleeding at the catheter site (n=3).

These results demonstrate that regadenoson is a potent and well-tolerated coronary vasodilator. The lack of any significant influence of the covariates on the PK and PD model parameters suggests a unit-based dosing for regadenoson.

EXAMPLE 3

Regadenoson is a selective $A_2$-adenosine receptor agonist under development for acute dilation of the coronary arterial vasculature during myocardial perfusion imaging. $A_{2A}$-adenosine receptor activation is reported to cause inhibition of platelet aggregation and neutrophil activation.

To characterize the drug more completely, in this study, we determined affinity and potency values for binding and for functional responses to regadenoson in preparations of human platelets and neutrophils (membranes and intact cells), CHO cells expressing human $A_{2A}$ receptors (membranes and intact cells), and rat brain striatal membranes. For comparison, parallel assays of responses to the reference $A_{2A}$ agonist CGS21680 were performed alongside each assay of regadenoson. Assay results are reported in Table 1 below.

TABLE 1

Values (mean ± SE) of affinity [Ki] and potency [EC$_{50}$ or IC$_{50}$] for regadenoson at A$_{2A}$-adenosine receptors

| Assay | Preparation | | | |
|---|---|---|---|---|
| | Human platelets | Human neutrophils | CHO hisA$_{2A}$-expressing | Rat striatum |
| Membrane Binding[1] | 534 ± 30 | 327 ± 14 | 347 ± 7 | 318 ± 5 |
| Membrane Binding[2] | | | 50 ± 4 | 43 ± 3 |
| Cell cAMP Content | 472 ± 17 | 406 ± 25 | 56 ± 4 | |
| Platelet Aggregation | 437 ± 44 | | | |
| Cell calcium Mobilization | 108 ± 8 | | | |
| Superoxide anion Production | | 328 ± 32 | | |

[1]displacement of binding of [3H]-ZM241385
[2]displacement of binding of [3H]-CG-S21680

Responses to regadenoson and to CGS21680 were similar in magnitude. In all assays, CGS21680 was slightly more potent than regadenoson (i.e., values of EC$_{50}$ for the 12 assays were 13-fold lower for CGS 21680, on average). It can be concluded from this study that regadenoson, like CGS21680, is not only a coronary vasodilator, but is also an inhibitor of both platelet aggregation and neutrophil activation (i.e., inflammation).

What is claimed is:

1. A method of producing coronary vasodilation with little peripheral vasodilation comprising administering to a human a single intravenous (iv) bolus dose of a pharmaceutical composition comprising regadenoson, a compound named (1-{9-[(4S, 2R,3R,5R)-3,4-dihydroxy-5-(hydroxymethyl)oxolan-2-yl]-6-aminopurin-2-yl}pyrazol-4-yl)-N-methylcarboxamide, which has the formula:

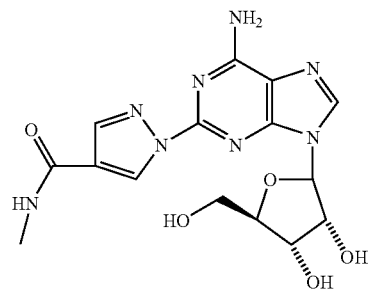

and at least one pharmaceutical excipient in an amount that is sufficient to increase the average coronary peak flow velocity by at least about 16.5 cm/sec.

2. The method of claim 1 wherein said single dose of a pharmaceutical composition is administered in about 10 to about 20 seconds.

3. The method of claim 1 wherein the amount of the single dose of a pharmaceutical composition administered is sufficient to raise the average coronary peak flow velocity by an amount ranging from about 16.5 to about 77.0 cm/sec.

4. The method of claim 1 wherein the single dose of pharmaceutical composition includes from about 10 to about 500 micrograms of regadenoson.

5. The method of claim 1 wherein the single dose of pharmaceutical composition includes an amount of regadenoson ranging from about 0.05 to about 60 μg/kg.

6. The method of claim 1 wherein myocardial perfusion imaging of a human is performed following administration of the single dose of the pharmaceutical composition to the human.

7. The method of claim 6 further comprising administering at least one radionuclide to the human at a time selected from the group consisting of before the human receives the dose of pharmaceutical composition, simultaneously with the administration of the dose of pharmaceutical composition or after administering the dose of pharmaceutical composition to the human.

8. The method of claim 6 wherein the radionuclide and the single dose of the pharmaceutical composition are administered separately to the human.

9. The method of claim 6 wherein the radionuclide and the single dose of the pharmaceutical composition are administered simultaneously to the human.

10. The method of claim 6 wherein the myocardium examination begins no sooner than about 1 minute from the time the single dose of the pharmaceutical composition is administered to the human.

* * * * *

UNITED STATES PATENT AND TRADEMARK OFFICE
CERTIFICATE OF CORRECTION

| | | |
|---|---|---|
| PATENT NO. | : 7,655,636 B2 | Page 1 of 1 |
| APPLICATION NO. | : 11/253322 | |
| DATED | : February 2, 2010 | |
| INVENTOR(S) | : Toufigh Gordi et al. | |

It is certified that error appears in the above-identified patent and that said Letters Patent is hereby corrected as shown below:

Column 8
Line 10, "(4S, 2R,3R,5R)" should be replaced with --(4S,2R,3R,5R)--.
Line 54, "method of claim 6" should be replaced with --method of claim 7--.
Line 57, "method of claim 6" should be replaced with --method of claim 7--.
Lines 60 and 61, "the myocardium examination" should be replaced with --myocardium examination--.

Signed and Sealed this
Eleventh Day of October, 2011

David J. Kappos
*Director of the United States Patent and Trademark Office*